United States Patent [19]
Walak

[11] Patent Number: 6,110,199
[45] Date of Patent: Aug. 29, 2000

[54] WELDING METHOD

[75] Inventor: Steven E. Walak, Natick, Mass.

[73] Assignee: Boston Scientific Corporation, Natick, Mass.

[21] Appl. No.: 09/366,885

[22] Filed: Aug. 4, 1999

Related U.S. Application Data

[62] Division of application No. 08/735,031, Oct. 22, 1996, Pat. No. 6,000,601.
[51] Int. Cl.[7] .............................. A61F 2/06; A61M 29/00
[52] U.S. Cl. ...................... 623/1.18; 623/1.15; 623/1.16; 623/1.27; 623/1.3; 623/1.2; 606/198; 606/195
[58] Field of Search .................................. 623/1.15, 1.16, 623/1.18, 1.3, 1.27, 1.2; 606/198, 195

[56] References Cited

U.S. PATENT DOCUMENTS

| | | | |
|---|---|---|---|
| 5,197,978 | 3/1993 | Hess | 623/1 |
| 5,354,308 | 10/1994 | Simon et al. | 606/198 |
| 5,395,390 | 3/1995 | Simon et al. | 606/198 |
| 5,735,893 | 4/1998 | Lau et al. | 623/1 |
| 5,817,152 | 10/1998 | Birdsall et al. | 623/1 |
| 6,000,601 | 12/1999 | Walak | 228/225 |

Primary Examiner—Michael J. Milano
Assistant Examiner—Hieu Phan
Attorney, Agent, or Firm—Vidas, Arrett & Steinkraus PA

[57] ABSTRACT

A welding method for improving the durability and strength of fusion weld joints in metal structures; the method is especially beneficial for metal structures fabricated from nickel-titanium alloy (nitinol) and for medical devices.

12 Claims, 2 Drawing Sheets

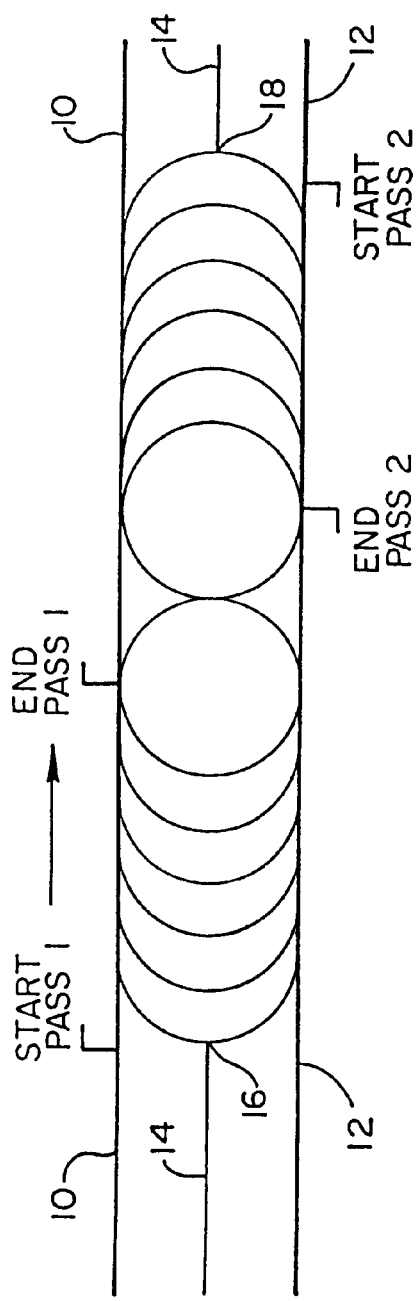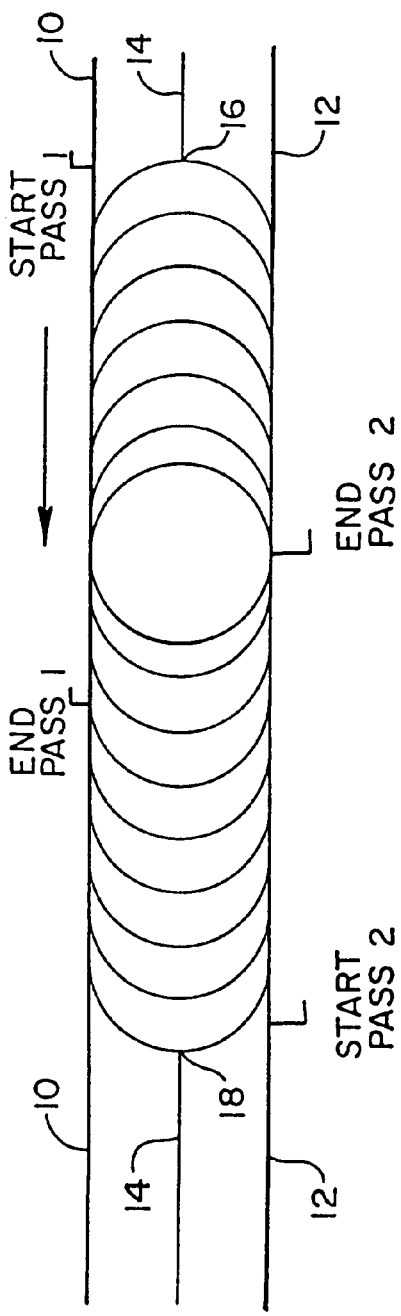

WELDING METHOD

RELATED APPLICATIONS

The present application is a divisional of application Ser. No. 08/735,031, filed Oct. 22, 1996, now U.S. Pat. No. 6,000,601 which is incorporated herein by reference in its entirety.

BACKGROUND OF THE INVENTION

Fusion welding techniques, such as laser welding, electron beam welding, tungsten inert gas welding, plasma welding and others, commonly leave a pool of molten metal at the end of the weld pass that solidifies after heat input to the weld has terminated. The terminal pool is commonly the weakest portion of the weld and is often the site of fracture initiation under moderate to low stress. Welds produced in nickel-titanium alloys (nitinol) are particularly prone to this problem.

SUMMARY OF THE INVENTION

The invention comprises a method of moving the location of the terminal pool in fusion welds to better accommodate high stress areas. This is accomplished by utilizing a multiple pass weld technique. The welding technique utilizes weld passes which initiate at remote portions of the area to be welded such as each end of a joint to be welded, and terminate within the interior of the weld area at or near a common meeting point. The multiple passes may overlap within the weld but overlap is not required. This technique is especially useful in devices having portions comprised of nitinol which require welding, such as in medical stents.

BRIEF DESCRIPTION OF THE FIGURES

Reference is made to the accompanying drawings in which illustrative embodiments of the invention are shown and from which the novel features and advantages of the invention will be apparent.

FIG. 1 is a schematic showing of a multiple pass method of welding according to the invention wherein the two passes meet at a common point.

FIG. 2 is similar to FIG. 1 showing overlap between the multiple passes.

DETAILED DESCRIPTION OF PREFERRED EMBODIMENTS OF THE INVENTION

Figure 3:
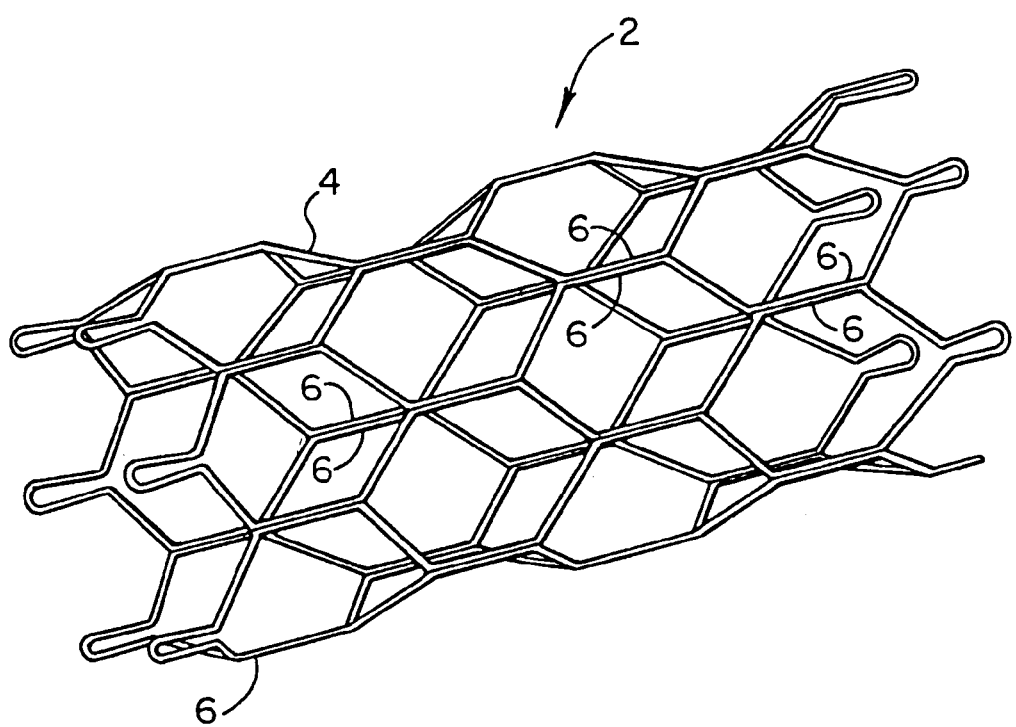
FIG. 3 is a perspective view of one form of stent which may make use of the invention.

Referring to FIGS. 1 and 2, it will be seen that a metal workpiece to be joined consisting of two elongate pieces 10 and 12 respectively brought into contact at 14 may be fusion welded according to the invention by two passes. Pass one starts as indicated (START PASS 1) at an outer portion 16 of a weld area and moves to the right in the Figure to end in a terminal pool as indicated at END PASS 1. A second pass (START PASS 2) begins at 18 and moves to the left in the Figure ending as indicated in a terminal pool at END PASS 2. In this embodiment the welding method utilizes two weld passes which initiate at each end of the joint and terminate within the interior of the weld joint the progression of the weld passes is shown schematically by the succession of circular areas.

FIG. 2 similarly uses two passes which move toward each other. However, they overlap as shown in the Figure where it can be seen that PASS 1 beginning at 16 and moving to the left in the Figure and PASS 2 beginning at 18 and moving to the right in the Figure can be seen to overlap within the weld to form a terminal pool.

For the purposes of this invention, as already indicated above, any of the various known forms of fusion welding may be utilized. Laser welding is presently most preferred. The passes may be sequential or simultaneous.

Referring to FIG. 3 it will be seen that an illustrative medical stent may include a skeletal frame generally indicated at 2, preferably formed from a single nitinol wire 4, bent to form a desired configuration. The wire 4 includes a plurality of abutting straight portions 6 which are joined to each other by welding utilizing the method described in FIGS. 1 or 2 above. As already pointed out, a nitinol stent especially benefits from this invention because nitinol stents are particularly prone to the problem of fracture initiation at the weld ends where terminal pools have been formed utilizing prior art welding techniques. The stent shown is fully disclosed in U.S. Pat. Nos. 5,354,308 and 5,395,390 and the entire content of both of these patents are incorporated herein by reference. The stent shown in FIG. 3 is shown here as an exemplary stent which may make use of the method of the invention although the method will find application in other stent configurations and in other metallic devices which require welding.

This disclosure is intended to be illustrative and not exhaustive. It will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A medical device, the medical device being implantable within the human body and being formed of a fusion weldable material shaped in a substantially tubular configuration, the medical device having bent sections axially adjacent to one another, said bent sections being connected by fusion welding forming a weld line, the weld line having a first initiation point and a second initiation point and a substantially centrally located region between the first initiation point and the second initiation point along the weld line, wherein the weld line extends substantially the length of the bent sections, the centrally located region being in a relatively lower stress region of the weld line as compared to the first and second initiation points, the weld line further comprising a terminal pool located in the centrally located region.

2. The medical device of claim 1, wherein the fusion weldable material comprises nitinol.

3. The medical device of claim 1, wherein the medical device is a wire metal stent, the stent being generally tubular and being expandable from a contracted stated to an expanded state.

4. The medical device of claim 3, wherein the terminal pool is located at point on the weld line equidistant from the initiation points.

5. The medical device of claim 1, formed by the method shaping and bending the fusion weldable material forming the substantially tubular configuration having the axially adjacent bent sections, coupling the adjacent bent section to form a work piece areas, the method further involving multiple passes comprising the steps of making a first fusion welding pass over a portion of a work piece area of the metal implantable medical device to be welded and making a second fusion welding pass over another portion of the work piece to be welded, thereby connecting the bent sections and forming the weld line, the two passes being directed toward each other and toward a common interior point whereby the terminal pool is formed in a low stress or non-critical area of the work piece area.

6. The medical device of claim 5, wherein the work piece area is a nitinol weld area.

7. The medical device of claim 5, wherein the medical device is a wire metal stent, the stent being generally tubular and being expandable from a contracted stated to an expanded state.

8. The medical device of claim 5 wherein the extent of the two passes mutually overlap at a common interior meeting point.

9. The medical device of claim 5 wherein the extent of the two passes ends substantially at a common interior meeting point.

10. The medical device of claim 5 wherein the two passes occur sequentially.

11. The medical device of claim 5 wherein the two passes occur simultaneously.

12. The medical device of claim 5, wherein the terminal pool is located at point on the weld line equidistant from the initiation points.

* * * * *